United States Patent
Iwasaka et al.

(10) Patent No.: US 6,878,159 B2
(45) Date of Patent: Apr. 12, 2005

(54) STENT

(75) Inventors: Masayuki Iwasaka, Tama (JP); Hitoshi Ishikawa, Hachoji (JP); Seiko Yunoki, Fussa (JP); Jun Iwami, Fujinomiya (JP); Makoto Takahashi, Fujinomiya (JP)

(73) Assignees: Olympus Corporation, Tokyo (JP); Terumo Kabushiki Kaisha, Tokyo (JP)

( * ) Notice: Subject to any disclaimer, the term of this patent is extended or adjusted under 35 U.S.C. 154(b) by 6 days.

(21) Appl. No.: 10/283,726

(22) Filed: Oct. 30, 2002

(65) Prior Publication Data

US 2003/0114922 A1 Jun. 19, 2003

(30) Foreign Application Priority Data

Oct. 30, 2001 (JP) .......................................... 2001-332876

(51) Int. Cl.[7] .................................................. A61F 2/06
(52) U.S. Cl. ....................................... 623/1.11; 623/1.16
(58) Field of Search ............................... 623/1.11–1.23, 623/1.32–1.33

(56) References Cited

U.S. PATENT DOCUMENTS

| | | |
|---|---|---|
| 5,176,626 A | 1/1993 | Soehendra |
| 5,443,458 A | 8/1995 | Eury |
| 5,474,563 A | 12/1995 | Myler et al. |
| 5,514,176 A | 5/1996 | Bosley, Jr. |
| 5,762,625 A | 6/1998 | Igaki |
| 6,357,104 B1 * | 3/2002 | Myers ...................... 29/527.1 |
| 6,369,355 B1 * | 4/2002 | Saunders ............... 219/121.71 |
| 6,485,509 B2 * | 11/2002 | Killion et al. ............. 623/1.15 |
| 6,673,102 B1 * | 1/2004 | Vonesh et al. ............. 623/1.13 |
| 6,673,103 B1 * | 1/2004 | Golds et al. ............... 623/1.13 |
| 2003/0114761 A1 * | 6/2003 | Brown ........................ 600/474 |
| 2003/0195616 A1 * | 10/2003 | Pinchasik et al. .......... 623/1.16 |

FOREIGN PATENT DOCUMENTS

| | | |
|---|---|---|
| EP | 0 423 916 A1 | 4/1991 |
| EP | 0 540 290 A2 | 5/1993 |
| EP | 0 716 836 A1 | 6/1996 |
| GB | 2 347 861 A | 9/2000 |
| JP | 8-196643 | 8/1996 |
| JP | 10-192411 | 7/1998 |
| WO | WO 92/11824 | 7/1992 |
| WO | WO 94/01056 | 1/1994 |
| WO | WO 94/12136 | 6/1994 |
| WO | WO 99/30641 | 6/1999 |

* cited by examiner

Primary Examiner—Corrine McDermott
Assistant Examiner—Suzette J-J. Gherbi
(74) Attorney, Agent, or Firm—Scully, Scott, Murphy & Presser

(57) ABSTRACT

A stent for dilating an internal lumen includes tubular segments that are arranged side by side in its axial direction. Each of segments expands and contracts in the diametrical direction of the stent, and its axial length is shorter than its expanded-state radius.

41 Claims, 8 Drawing Sheets

STENT

CROSS-REFERENCE TO RELATED APPLICATIONS

This application is based upon and claims the benefit of priority from the prior Japanese Patent Application No. 2001-332876, filed Oct. 30, 2001, the entire contents of which are incorporated herein by reference.

BACKGROUND OF THE INVENTION

1. Field of the Invention

The present invention relates to a stent for dilating an internal lumen.

2. Description of the Related Art

Methods for recovering an indwelling stent are described in Jpn. Pat. Appln. KOKAI Publication No. 10-192411 and U.S. Pat. No. 5,474,563, for example. In these methods, the opposite ends of the stent are axially pulled in opposite directions to contract the stent diametrically inward as the stent is separated from an internal lumen and recovered. Described in European Patent Application Publication No. 423,916 is a method in which a stent is drawn out and recovered with its proximal end side contracted diametrically inward.

In many cases, tumors cause constriction of lumens, especially the lumen of a pancreatic or biliary duct system. If a stent is indwelled in one such lumen for a long period of time, the mucous membrane of the lumen may possibly grow into the stent through its stitches or adhere to the mucous membrane.

In recovering the indwelling stent, therefore, it must be separated from the mucous membrane. In the case where the indwelling stent is of a self-expansion type, it is pressed against the mucous membrane in the lumen, making it difficult to be drawn out for recovery.

BRIEF SUMMARY OF THE INVENTION

The present invention is to provide a stent capable of being easily recovered from a lumen.

According to an aspect of the invention, a stent for dilating an internal lumen according to an aspect of the invention comprises tubular segments capable of expanding and contracting in the axial direction thereof and having an axial length shorter than the expanded-state radius thereof, the segments being arranged side by side from the distal side to the proximal side in the axial direction.

Additional and advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 4A to 4C are formed and the respective names of the loops in this state;

DETAILED DESCRIPTION OF THE INVENTION

Preferred embodiments of the present invention will now be described with reference to the accompanying drawings.

Figure 1A:
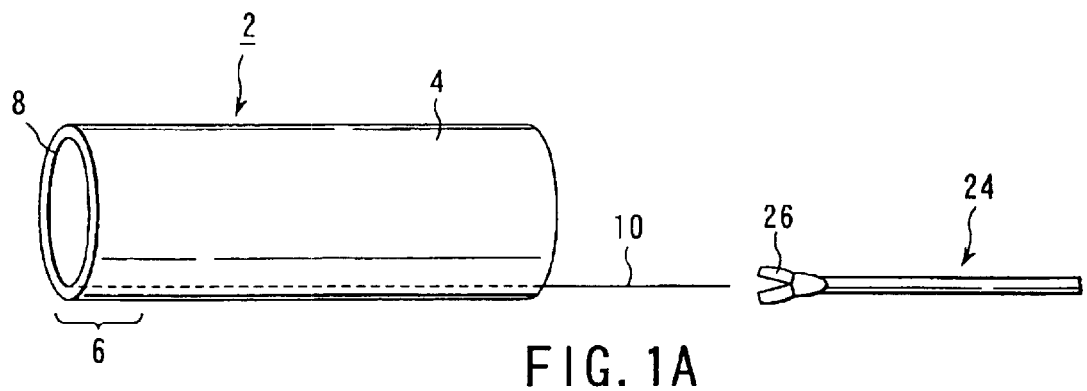
FIG. 1A is a schematic perspective view showing a stent according to a first embodiment of the invention indwelled in a lumen.

A first embodiment will first be described with reference to FIGS. 1A to 3B. As shown in FIG. 1A, a stent 2 according to this embodiment includes a tubular member 4, preferably in the form of a hollow cylinder, a looped member 8 twined in a distal end 6 of the tubular member 4, and a pull thread 10 connected to the looped member 8. The looped member 8 can be expanded or contracted in its diametrical direction. The pull thread 10 further extends to the distal side through the bore of the tubular member 4.

Figure 2B:
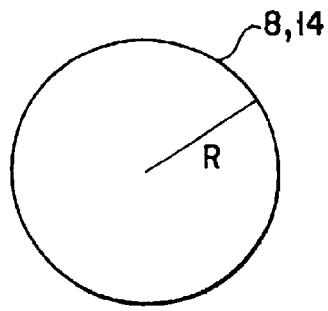
FIG. 2B is a side view of the stent shown in FIG. 2A.
Figure 2A:
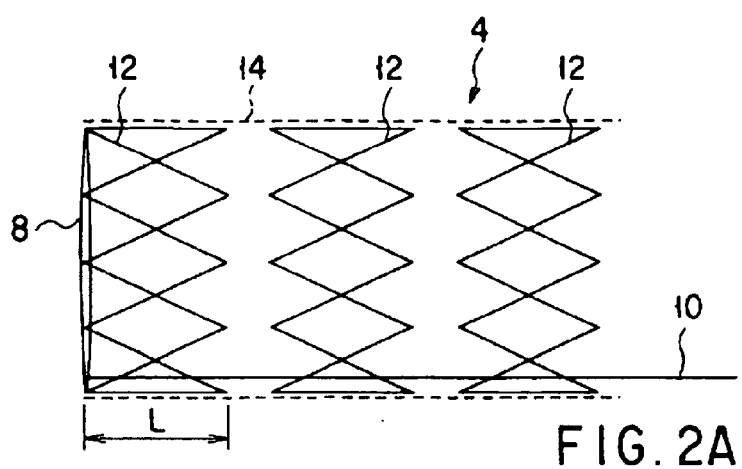
FIG. 2A is a schematic front view of a tubular member showing the stent according to the first embodiment indwelled in the lumen.

In the tubular member 4, as shown in FIG. 2A, tubular segments 12 that are each formed of a wire are arranged side by side in the axial direction. A tubular filmy member 14 that is expansible in its diametrical direction is fixed on the segment assembly 12. Each segment 12 has a force to expand outward in the diametrical direction, and can contract inward in the diametrical direction. Thus, the filmy member 14 is expanded and contracted in the diametrical direction as the segment assembly 12 expand and contract. Preferably, each segment 12 is formed by zigzagging a wire of a metallic material, elastic resin material, or organic material. The axial length of each segment assembly 12 is L, which is shorter than a radius R (see FIG. 2B) of the segment assembly 12 in a diametrically expanded state. The length L and the radius R change as the segment assembly 12 expands and contracts. As shown in FIG. 2A, the looped member 8 is twined in the distal end 6 of the segment 12 on the extreme distal side, and is connected to the leading end (distal end) 6 of the filmy member 14 by adhesive bonding, for example.

Figure 3A:
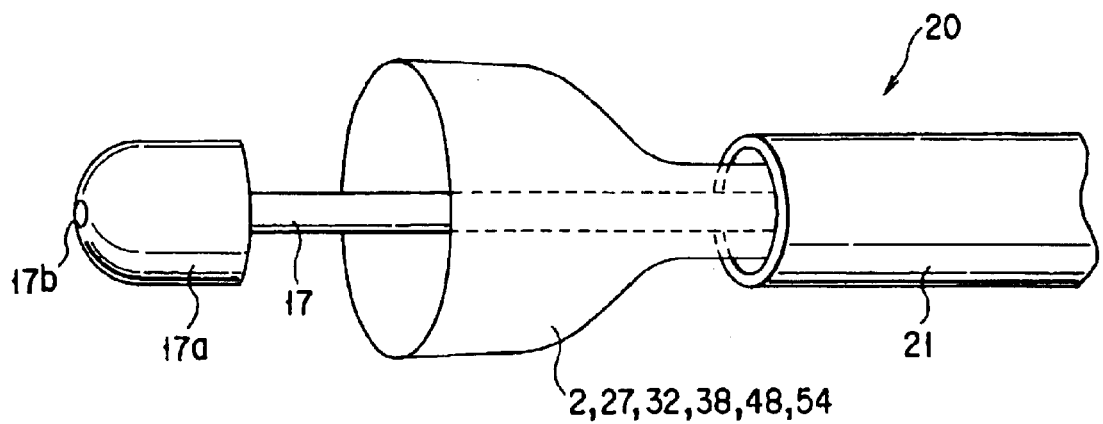
FIG. 3A is a schematic view showing a stent delivery system.

The stent 2 can be indwelled in a narrow segment 22 in an internal lumen in the following manner by using a stent delivery system 20, for example. As shown in FIG. 3A, the stent delivery system 20 is composed of an inner catheter 17 having a hemispherical protuberance 17a and an outer sheath 21 that covers the periphery of the catheter 17. The outside diameter of the protuberance 17a is substantially equal to that of the outer sheath 21. The protuberance 17a has a through hole 17b that opens into the bore of the inner catheter 17. Preferably, a guide wire (not shown) or the like should be able to be passed forward through the hole 17b. The outer sheath 21 can move relatively to the inner catheter 17 in the axial direction of the catheter 17.

The stent 2 is reduced in diameter and held between the outer periphery of the inner catheter 17 and the inner periphery of the outer sheath 21. As the tubular member 4 is then pressed diametrically inward, the segment assembly 12, along with the filmy member 14, is contracted diametrically inward. The hand-side portion of the pull thread 10 is located on the proximal end side of the stent delivery system 20. If the outer sheath 21 is pulled relatively to the inner catheter 17 to the hand side with the distal end of the stent 2 thus situated near the protuberance 17a, the stent 2 is rendered gradually self-expanded from its leading end toward its trailing end by means of the diametrically outward expanding force of the segment assembly 12, as shown in FIGS. 3A and 3B.

Figure 3B:
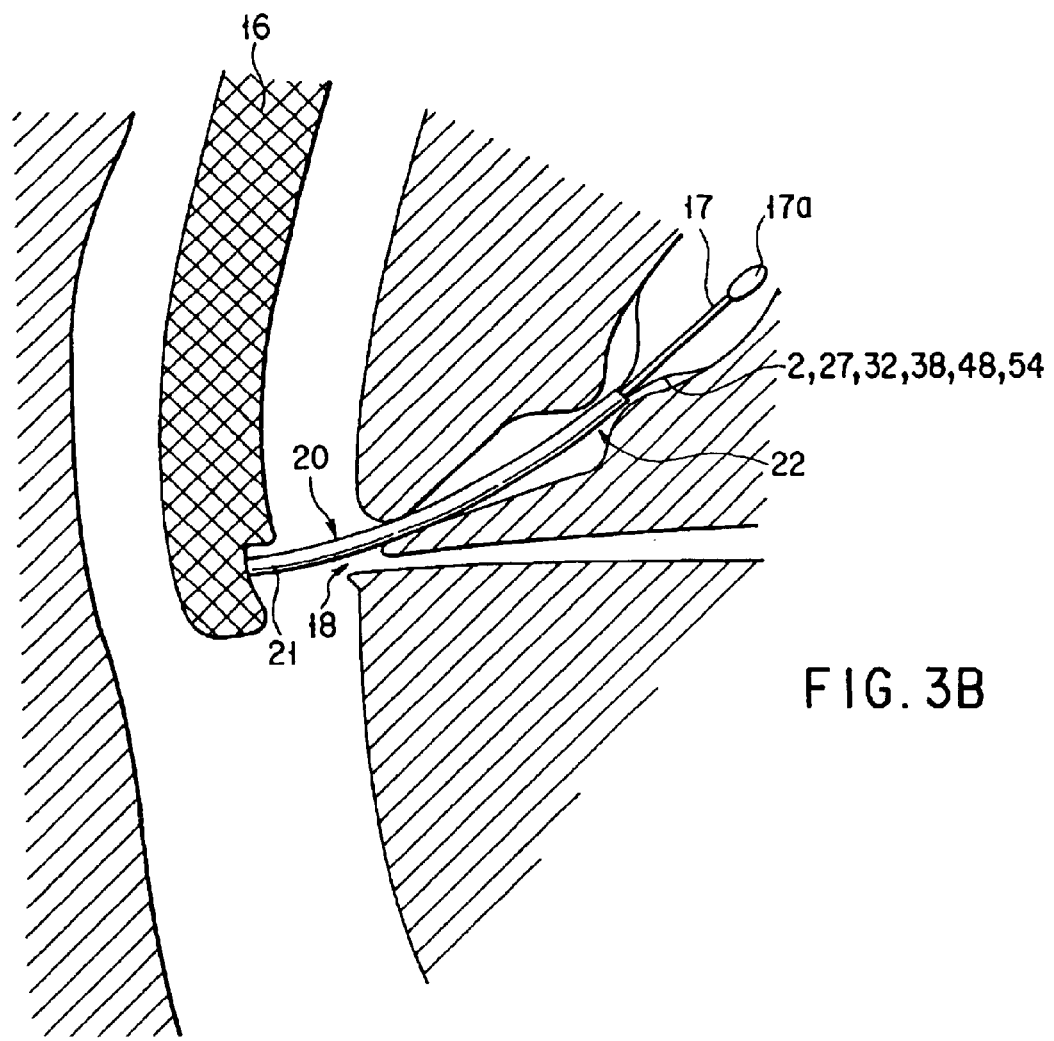
FIG. 3B is a schematic view showing the way the stent of FIG. 1A is orally guided to a duodenal papilla by means of an endoscope.

As shown in FIG. 3B, the stent delivery system 20 thus fitted with the stent 2 is caused orally to reach a duodenal papilla 18 through a channel of a lateral-view endoscope 16, for example. The protuberance 17a of the stent delivery system 20 is further introduced into the inner part of the narrow segment 22 so that the system 20 is brought to a position just ahead of the narrow segment 22 in the lumen.

If the outer sheath 21 of the stent delivery system 20 is pulled relatively to the inner catheter 17 to the hand side in this state, the stent 2 is rendered self-expanded outward from its leading end in the diametrical direction of the lumen, whereby the narrow segment 22 is expanded gradually. The outer sheath 21 is further pulled to expand the stent 2 to its proximal end, thereby expanding the narrow segment 22 to form a wide passage in the lumen. Thereafter, the inner catheter 17 is pulled and taken out to the hand side through the bore of the stent 2 (segment assembly 12). If the stent 2 is released from the stent delivery system 20, therefore, it is rendered self-expanded outward from its leading end in the diametrical direction of the lumen, and indwelled in the narrow segment 22 in a dilated state. Thus, the stent 2 presses the inner wall (mucous membrane) in the lumen, thereby dilating the lumen diametrically outward.

Figure 1B:
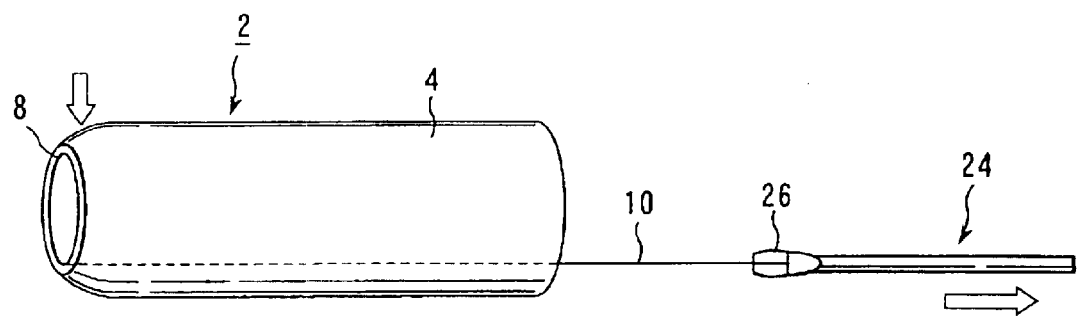
FIG. 1B is a schematic perspective view showing a process for turning the stent of FIG. 1A inside out by means of a holding forceps.
Figure 1C:
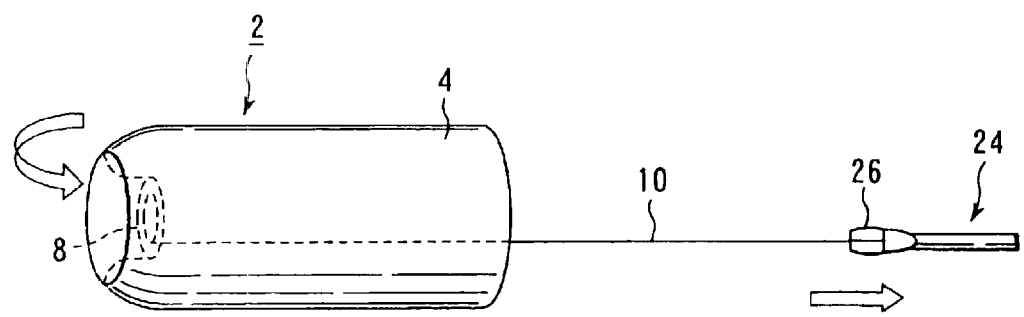
FIG. 1C is a schematic perspective view showing a process in which the stent of FIG. 1B is further turned back.
Figure 2D:
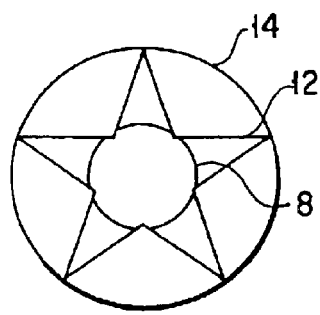
FIG. 2D is a side view of the stent shown in FIG. 2C.
Figure 2C:
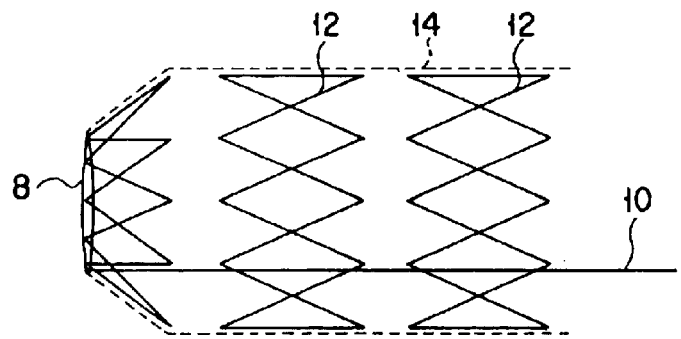
FIG. 2C is a schematic front view of the tubular member showing a process for turning the stent of FIGS. 2A and 2B inside out.

The following is a description of processes for recovering the stent 2 expanded in this manner. The pull thread 10 of the stent 2 indwelled in the state shown in FIG. 1A is held by means of a forceps portion 26 of a holding forceps 24, for example, and pulled to the hand side, as shown in FIG. 1B. The looped member 8 is gradually contracted inward in the diametrical direction of the stent 2, as shown in FIGS. 1B and 2C. If the pull thread 10 is further pulled, the looped member 8 and the distal end 6, which are contracted diametrically inward, are drawn into the stent 2, as shown in FIG. 1C. Finally, the stent 2 is turned inside out as it is separated diametrically inward from the lumen (narrow segment 22) and recovered.

The movement of the segment 12 on the side of the distal end 6 in this state, in particular, will be described with reference to FIGS. 2A to 2H.

Figure 2F:
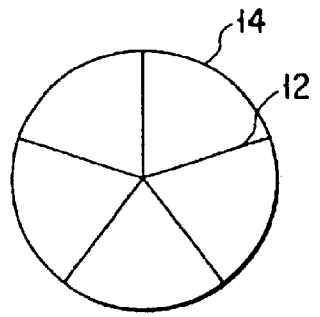
FIG. 2F is a side view of the stent shown in FIG. 2E.
Figure 2E:
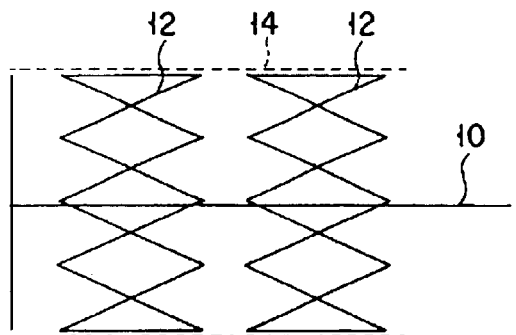
FIG. 2E is a schematic front view of the tubular member showing a process in which the stent of FIGS. 2C and 2D is further turned back.
Figure 2H:
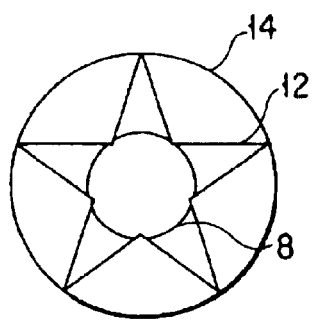
FIG. 2H is a side view of the stent shown in FIG. 2G.
Figure 2G:
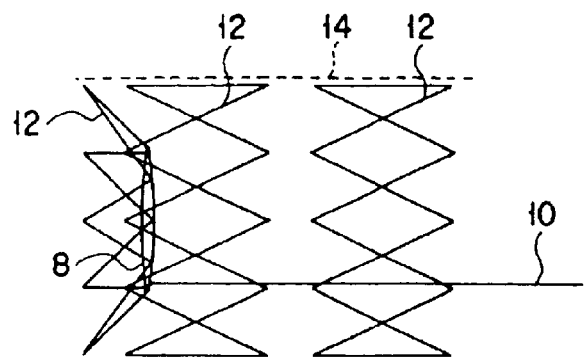
FIG. 2G is a schematic front view of the tubular member showing a process in which the stent of FIGS. 2E and 2F is turned back.

FIG. 2A, like FIG. 1A, shows the stent 2 indwelled in the lumen. If the pull thread 10 is pulled to the hand side, the looped member 8 starts to diminish diametrically inward, and the segment 12 on the distal side starts to contract diametrically inward, as shown in FIGS. 2C and 2D, as in FIG. 1B. If the pull thread 10 is pulled further, the looped member 8 is further contracted diametrically inward, and the segment 12 on the distal side is folded in, as shown in FIGS. 2E and 2F. If the pull thread 10 is pulled further, the looped member 8 and the extreme distal-side segment 12, contracted diametrically inward, are gradually turned inside out as they are drawn into the adjacent segments 12 on the proximal side. As this is done, the axial length L of each segment 12 is shorter than the radius R of each expanded segment 12, and the adjacent zigzag segments 12 cannot easily interfere with one another as they are turned inside out in the state shown in FIGS. 2E and 2G.

If the pull thread 10 is further pulled, the segment 12 next to the extreme-end segment 12 is turned inside out in the same manner as the end segment 12 as it is drawn into the adjacent segments 12 on the proximal side. The segments 12 arranged on the distal side are successively drawn into the adjacent segments 12 on the proximal side in this manner. Then, the whole stent 2 is turned inside out as it is separated diametrically inward from the inner wall (mucous membrane) in the lumen, and is taken out and recovered from the narrow segment 22.

In recovering the stent 2 of FIGS. 1A and 2A that is indwelled in the narrow segment 22 in the lumen, therefore, the stent 2 is gradually separated inward in the diametrical direction or in the direction perpendicular to the mucous membrane from the side of the distal end 6. Thus, the possibility of the stent 2 rubbing against the mucous membrane in the lumen can be lowered even in an initial stage of turning the stent 2 inside out, so that a burden on the lumen can be lightened. As the separation from the mucous membrane advances, the area of contact between the stent 2 and the mucous membrane decreases. Even in case the stent 2 heavily adheres to the mucous membrane, therefore, it can be separated and recovered relatively easily.

In the stent 2 according to this embodiment, the pull thread 10 may be located in the duodenal papilla 18 or extend to the duodenum so that it can be recognized through the endoscope 16. Further, a ball (not shown) or the like may be attached to the proximal side of the pull thread 10 so that a satisfactory drawing force can be applied to the holding forceps that holds the thread.

The pull thread 10 should preferably be formed of a high-resistance material that stands the drawing force, such as a metallic wire, polyamide-based plastic fiber thread (string), or silk thread. The filmy member 14 should preferably be formed of a thin, tear-resistant material, e.g., an elastic resin or organic material, such as a fluoroplastic, silicone, or urethane resin. The filmy member 14 may be made of bio-absorbable and biodegradable material, such as polymers of polylactic acid or polyglycolic acid.

Figure 4A:
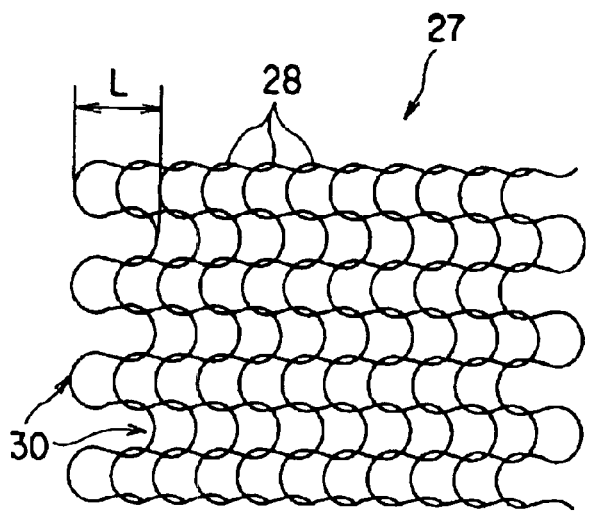
FIG. 4A is a schematic front view taken from the outside, showing a wire of a stent having a plain-stitch structure according to a second embodiment.
Figure 4B:
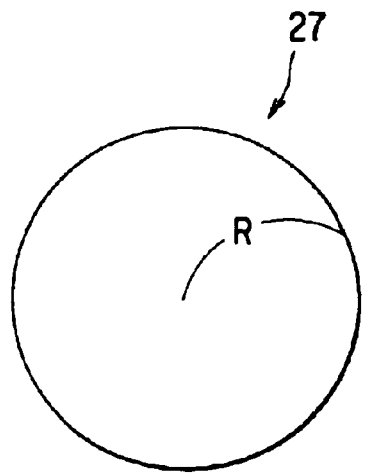
FIG. 4B is a side view corresponding to FIG. 4A.
Figure 4C:
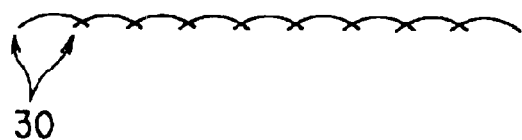
FIG. 4C is an axial sectional view corresponding to FIG. 4A.
Figure 5:
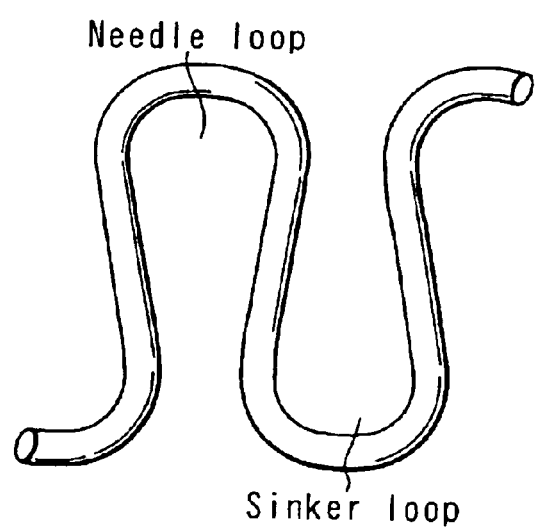
FIG. 5 is a schematic view showing the way loops shown

A second embodiment will now be described with reference to FIGS. 4A to 8E. As shown in FIGS. 4A to 4C, a tubular member of a stent 27 according to this embodiment is formed of a wire that has a plain-stitch structure. Each tier of stitches corresponds to one segment 28. The segments 28 are tied to form a tube type segment assembly. As shown in FIG. 5, a loop is formed of a needle loop and a sinker loop. The needle loop is a loop that is formed in the wire by means of a needle (not shown). The sinker loop is a loop that is formed as the needle loop is formed. As shown in FIG. 4A, the axial length of each segment 28 is represented by L. The length L is shorter than the radius R of each segment 28 that is expanded in the axial direction (see FIGS. 4A and 4B).

Preferably, the plain-stitched segment assembly 28 is covered by a filmy member (not shown). The filmy member can freely expand and contract in its diametrical direction. Preferably, this wire is formed of a superelastic alloy or shape-memory alloy, and can freely expand and contract in its diametrical direction.

Figure 6A:
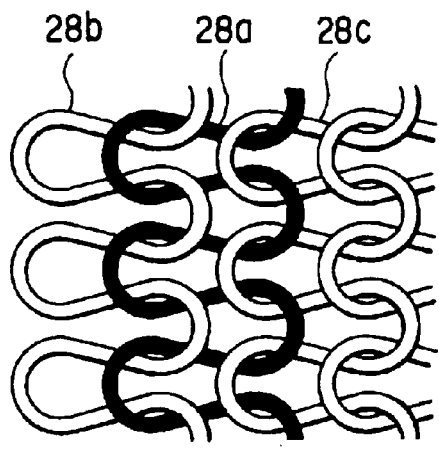
FIG. 6A is a schematic view showing reverse-side loops of the plain-stitched wire of the stent according to the second embodiment.
Figure 6B:
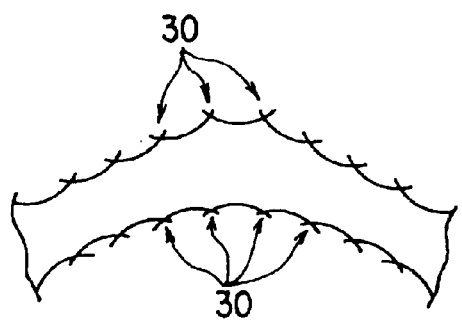
FIG. 6B is an axial sectional view of the wire of FIG. 6A bent in the lumen.

As shown in FIGS. 6A and 6B, the plain-stitched segments 28 are arranged so that the reverse-side loop of each plain stitch faces outward. In this stitch structure, as shown in FIG. 6A, the needle loops of a segment 28a in a certain tier are hooked on the outside of the needle loops of a segment 28b in the next tier ahead. Further, the sinker loops of the segment 28a are hooked on the outside of the sinker loops of a segment 28c in the next tier behind. The sinker loops of the segment 28a are arranged so that they are led from inside to outside through the sinker loops of the segment 28b in the next tier ahead to be hooked on the outside of the needle loops. Thus, a needle loop in a certain position never fails to be hooked on the outside of a needle loop in the next tier ahead, while a sinker loop never fails to be hooked on a sinker loop in the next tier behind from outside.

As shown in FIG. 6B, therefore, engaging portions 30 between the segment 28a in each certain tier of the stitch structure shown in FIG. 6A and the segments 28b and 28c in the next tiers ahead and behind are arranged facing outward, as shown in FIG. 6B.

Figure 7A:
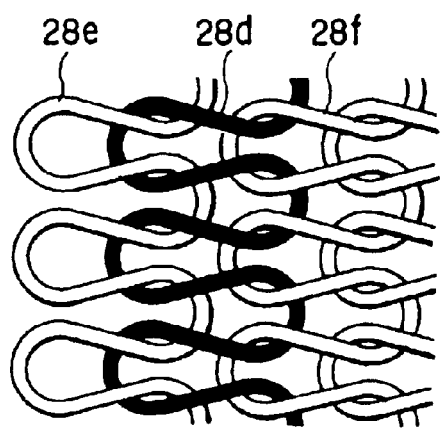
FIG. 7A is a schematic view showing face-side loops of a plain-stitched wire of a prior art stent.

As shown in FIG. 7A, moreover, the prior art plain-stitched wire has a structure such that the face-side loop of each plain stitch faces outward. In this stitch structure, as shown in FIG. 7A, the needle loops of a segment 28d in a certain tier are hooked on the inside of the needle loops of a segment 28e in the next tier ahead. Further, the sinker loops of the segment 28d are hooked on the inside of the sinker loops of a segment 28f in the next tier behind. The sinker loops of the segment 28d are arranged so that they are led from outside to inside through the outside of the sinker loops of the segment 28e in the next tier ahead to be hooked on the inside of the needle loops. Thus, a needle loop in a certain position never fails to be hooked on the inside of a needle loop in the next tier ahead, while a sinker loop never fails to be hooked on a sinker loop in the next tier behind from inside.

Figure 7B:
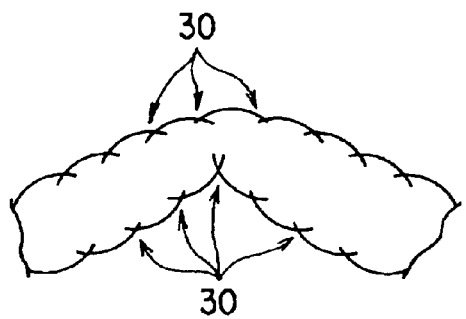
FIG. 7B is an axial sectional view of the wire of FIG. 7A bent in the lumen.

As shown in FIG. 7B, therefore, engaging portions 30 between the segment 28d in each certain tier of the stitch structure shown in FIG. 7A and the segments 28e and 28f in the next tiers ahead and behind are arranged facing inward, as shown in FIG. 7B. If the stent formed of segment assembly 28 is bent, its bore is collapsed so that its inside diameter inevitably becomes smaller than when in the expanded state.

In the stent 27 according to this embodiment shown in FIG. 6B, on the other hand, the engaging portions 30 face outward. If the stent 27 is bent, therefore, its inside diameter can be kept at its normal-state value or made greater. If the reverse-side loop structure is made to face outward, as shown in FIG. 6B, therefore, the stent 27 cannot be easily changed in diameter when it is bent. Thus, a constant diameter can be maintained in the lumen.

The stent 27, like the stent 2 according to the embodiment, can be indwelled in the lumen. The inner catheter 17 of the stent delivery system 20 shown in FIG. 3A is inserted into the stent 27. In the case where the stent 27 is fitted in the outer sheath 21, the plain-stitched segments 28, along with the filmy member, are pressed and contracted diametrically inward. If the stent 27 is released from the stent delivery system 20, as shown in FIG. 3A, it is rendered self-expanded outward in the diametrical direction of the lumen and indwelled in the narrow segment 22 in a dilated state, as shown in FIG. 3B. Thus, the stent 27 presses the inner wall (mucous membrane) in the lumen, thereby dilating the lumen diametrically outward.

Figure 8A:
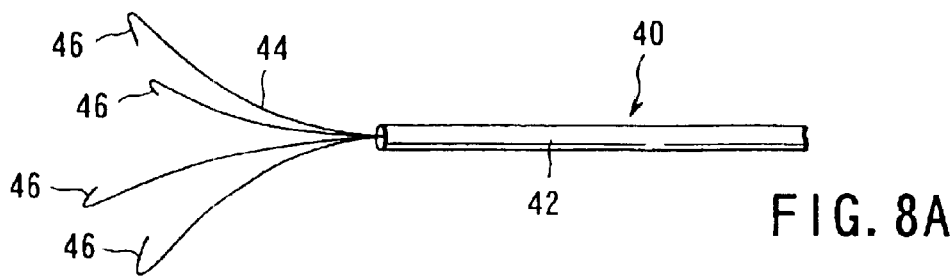
FIG. 8A is a schematic perspective view showing a holding forceps for stent recovery according to the second embodiment.

The following is a description of processes for recovering the stent 27 expanded in this manner. In this case, a holding forceps 40 for stent recovery is used, as shown in FIG. 8A. The holding forceps 40 is composed of a sheath 42 and holding portions 44 that project from the distal end of the sheath 42 and are spreadable in the diametrical direction and retractable in the axial direction. The distal end of each holding portion 44 is provided with a return portion 46 that can be hooked on the segments 28 of the stent 27 that has the stitch structure inside. The return portions 46 have a moderate curvature to avoid damage to the mucous membrane. The stent 27 is indwelled in the same manner as the stent 2 according to the first embodiment.

Figure 8B:
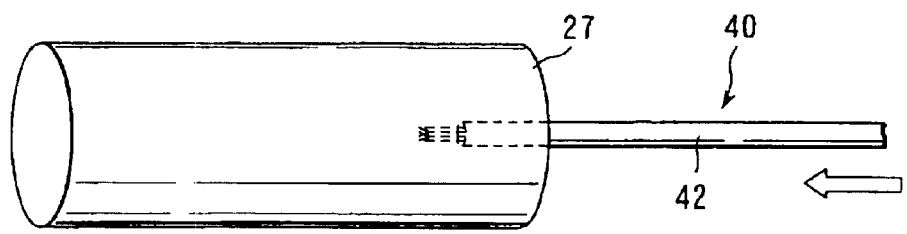
FIG. 8B is a schematic perspective view showing the way the holding forceps of FIG. 8A is inserted into the stent indwelled in the lumen.
Figure 8C:
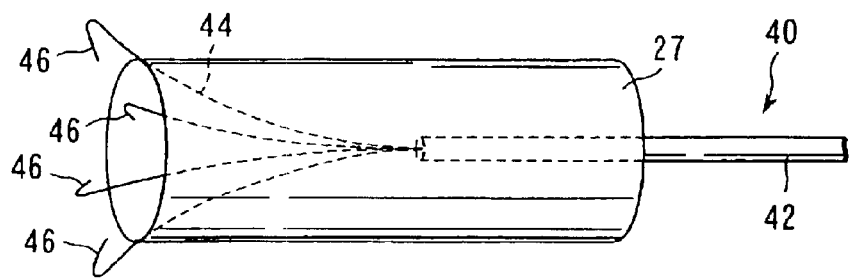
FIG. 8C is a schematic perspective view showing the way a forceps portion of the holding forceps are spread and passed through the stent of FIG. 8B from inside to outside.

First, the holding forceps 40 is inserted axially into the stent 27, as shown in FIG. 8B. Then, the holding portions 44 of the holding forceps 40 are stretched forward and spread, passed outward through the stitches of the segment 28 on the inner wall on the distal end side of the stent 27 from the inside, and brought to the outside of the filmy member, as shown in FIG. 8C.

Figure 8D:
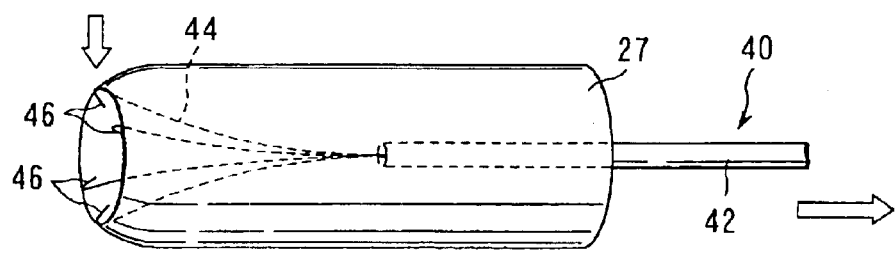
FIG. 8D is a schematic perspective view showing the way the holding forceps of FIG. 8C is closed so that return portions are hooked on stitches of the stent.
Figure 8E:
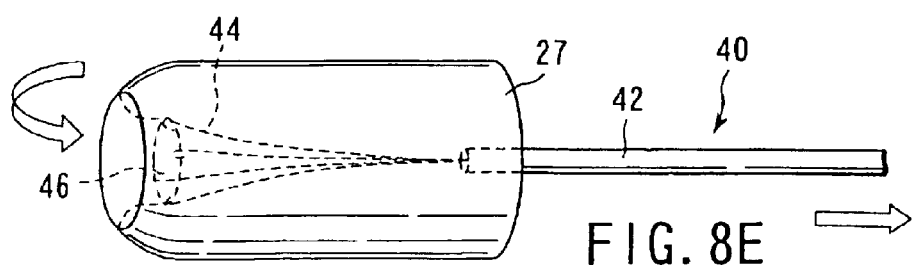
FIG. 8E is a schematic perspective view showing the way the distal end of the stent is diametrically contracted as it is returned to the proximal end side.

Then, the holding portions 44 are fully spread so that the return portions 46 are located entirely outside the filmy member. Thereafter, the holding forceps 40 is pulled backward to close the holding portions 44, whereupon the return portions 46 are hooked on the distal-side segment 28, as shown in FIG. 8D. After it is confirmed that the return portions 46 are hooked on the distal end side of the stent 27, the holding portions 44 are further closed. As shown in FIG. 8E, the distal side of the stent 27 is contracted diametrically inward as it is pulled back to the proximal side, whereupon the distal side of the stent 27 is drawn into the stent 27. The stent 27 is further drawn into itself, and the whole stent 27 is turned inside out as it is separated diametrically inward from the inner wall (mucous membrane) in the lumen (narrow segment 22). Thus, the stent 27 can be recovered.

In recovering the stent 27 of FIGS. 4A to 8E that is indwelled in the lumen, therefore, the stent 27 is gradually separated inward in the direction perpendicular to the mucous membrane from the distal side. Thus, the possibility of the stent 27 rubbing against the mucous membrane in the lumen can be lowered in an initial stage of turning the stent 27 inside out, so that the burden on the lumen can be lightened. As the separation from the mucous membrane advances, the area of contact between the stent 27 and the mucous membrane decreases. Even if the stent 27 heavily adheres to the mucous membrane, therefore, it can be separated and recovered relatively easily.

The holding forceps 40 for stent recovery may be a four-prong holding forceps, as shown in FIG. 8A. Alternatively, however, it may be a three- or five-prong holding forceps, for example. The return portions 46 are larger than the stitches of the segments 28 of the stent 27. If the return portions 46 are pulled back after they are once passed through the stitches, therefore, it is hard for them to pass through the same stitches and be disengaged. Thus, the holding forceps 40 can satisfactorily hold the stent 27 and recover it with ease. Preferably, the filmy member should be removably attached to the plain-stitched segments 28 so as to cover them. However, it is not essential.

Figure 9A:
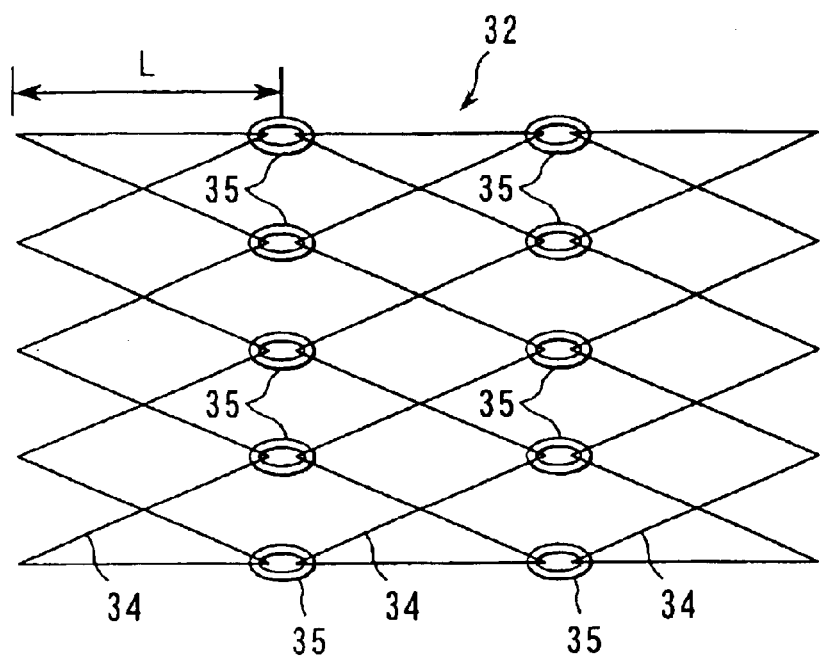
FIG. 9A is a schematic view showing a wire according to a third embodiment used in the stent according to the second embodiment.
Figure 9B:
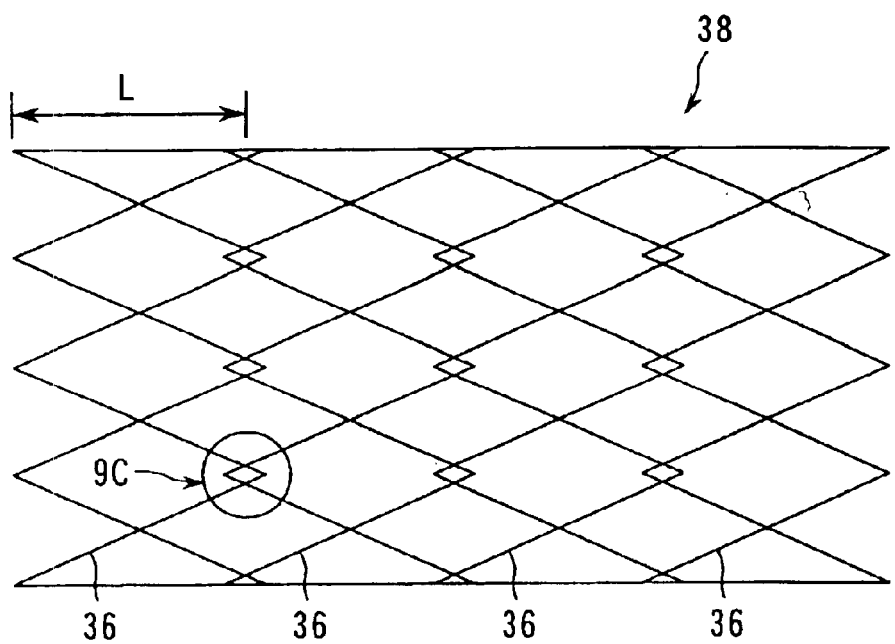
FIG. 9B is a schematic view showing another wire according to the third embodiment used in the stent according to the second embodiment.
Figure 9C:
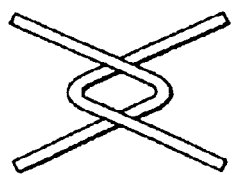
FIG. 9C is an enlarged view of a portion 9C shown in FIG. 9B.

A third embodiment will now be described with reference to FIGS. 9A to 9C. This embodiment is a modification of the first and second embodiments. As shown in FIG. 9A, a tubular member of a stent 32 according to this embodiment comprises tubular segments 34 that are each formed of a zigzagged wire and are arranged side by side in the axial direction. The adjacent segments 34 are connected to one another by means of string or rubber band connecting members 35. The segment assembly 34 can freely expand and contract in diametrical and axial directions. The axial length L of each segment 34 is shorter than its diametrically-expanded-state radius R.

The stent 32, like the stents 2 and 27 according to the first and second embodiments, can be indwelled in the lumen.

The inner catheter 17 of the stent delivery system 20 shown in FIG. 3A is inserted into the stent 32. If the stent 32 is fitted in the outer sheath 21, the segments 34 are pressed and contracted diametrically inward. If the stent 32 is released from the stent delivery system 20, as shown in FIG. 3A, it is rendered self-expanded outward in the diametrical direction of the lumen and indwelled in the narrow segment 22 in a dilated state, as shown in FIG. 3B. Thus, the stent 32 presses the inner wall (mucous membrane) in the lumen, thereby dilating the lumen diametrically outward.

Since the stent 32 can be recovered in the same manner as the stent 27 according to the second embodiment, a description of its recovery is omitted.

In recovering the stent 32 of this embodiment shown in FIG. 9A that is indwelled in the lumen, as in the case of the second embodiment, therefore, the stent 32 is gradually separated in the direction perpendicular to the mucous membrane from the distal end side. Thus, the possibility of the stent 32 rubbing against the mucous membrane in the lumen can be lowered in an initial stage of turning the stent 32 inside out, so that the burden on the lumen can be lightened. As the separation from the mucous membrane advances, the area of contact between the stent 32 and the mucous membrane decreases. Even if the stent 32 strongly adheres to the mucous membrane, therefore, it can be separated and recovered relatively easily.

According to this embodiment, the string or rubber band connecting members 35 are used to connect the segments 34 to one another. Alternatively, however, a stent 38 may be formed in a manner such that each wire that constitutes a segment is connected to and across wires that constitute its adjacent segments 36, as shown in FIG. 9B and in the enlarged view of FIG. 9C that illustrates the portion 9C in FIG. 9B.

Figure 10B:
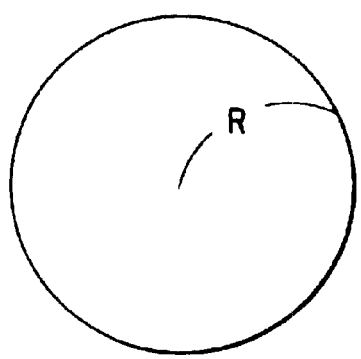
FIG. 10B is a side view of the stent shown in FIG. 10A.
Figure 10A:
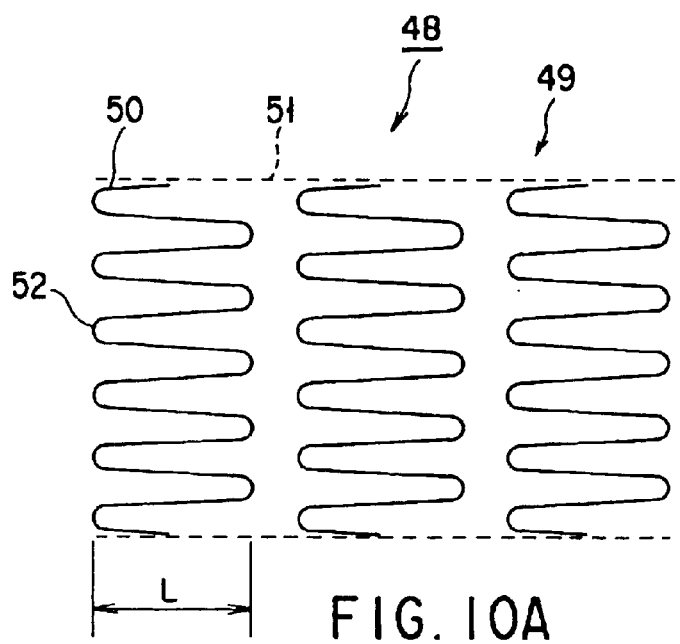
FIG. 10A is a front view showing a stent according to a fourth embodiment in a state such that segments formed of wires waved in the form of a tube are each arranged side by side and covered with a filmy member.

A fourth embodiment will now be described with reference to FIGS. 10A and 10B. This embodiment is a modification of the second embodiment. As shown in FIG. 10A, a tubular member 49 of a stent 48 according to this embodiment is composed of segment assembly 50, each of segments 50 composed of a tube of a wavy wire, and a filmy member 51 that can freely expand and contract in the diametrical direction and covering the segment assembly 50, each of segments 50 arranged side by side. The segment assembly 50 can freely contract and expand in the diametrical direction. As shown in FIGS. 10A and 10B, the axial length L of each of segments 50 is shorter than its diametrically-expanded-state radius R.

The stent 48, like the stent 27 according to the second embodiment, can be indwelled in the lumen. The inner catheter 17 of the stent delivery system 20 shown in FIG. 3A is inserted into the stent 48. In the case where the stent 48 is fitted in the outer sheath 21, the tubular member 49 is pressed and contracted diametrically inward. If the stent 48 is released from the stent delivery system 20, as shown in FIG. 3A, it is rendered self-expanded outward in the diametrical direction of the lumen and indwelled in the narrow segment 22 in a dilated state, as shown in FIG. 3B. Thus, the stent 48 presses the inner wall (mucous membrane) in the lumen, thereby dilating the lumen diametrically outward.

Since the stent 48 can be recovered in the same manner as the stent 27 according to the second embodiment, a description of its recovery is omitted.

In recovering the stent 48 of this embodiment shown in FIG. 10A that is indwelled in the lumen, as in the case of the second embodiment, therefore, the stent 48 is gradually separated in the direction perpendicular to the mucous membrane from the distal end side. Thus, the possibility of the stent 48 rubbing against the mucous membrane in the lumen can be lowered in an initial stage of turning the stent 48 inside out, so that the burden on the lumen can be lightened. As the separation from the mucous membrane advances, the area of contact between the stent 48 and the mucous membrane decreases. Even if the stent 48 strongly adheres to the mucous membrane, therefore, it can be separated and recovered relatively easily. Since its distal end portion 52 is not pointed, moreover, the stent 48 can be readily recovered without easily catching and damaging the mucous membrane in the lumen.

A fifth embodiment will now be described with reference to FIGS. 11A and 11B. This embodiment is a modification of the second embodiment. Usually, a wire having a plain-stitch structure is formed so that face-side loops appear on its outer peripheral surface, as shown in FIG. 7B. After this wire is turned inside out so that the reverse-side loops shown in FIG. 6B appear on its outer peripheral surface, the filmy member is provided on the outer peripheral surface of the wire to realize the second embodiment. In this case, a stent 54 is urged to return to a state such that face-side loops 60 such as the ones shown in FIG. 7B appear on its outer peripheral surface. Accordingly, there is the possibility of the stent 54 being gradually outwardly turned inside out from its end portion and then turned entire only when it is subjected to a small shock or the like in a non-loaded state. Thus, there is the possibility of the stent 54 being turned from a state such that reverse-side loops 62 face outward, as shown in FIG. 11B, to a state such that the face-side loops 60 face outward, as shown in FIG. 11A.

Figure 11A:
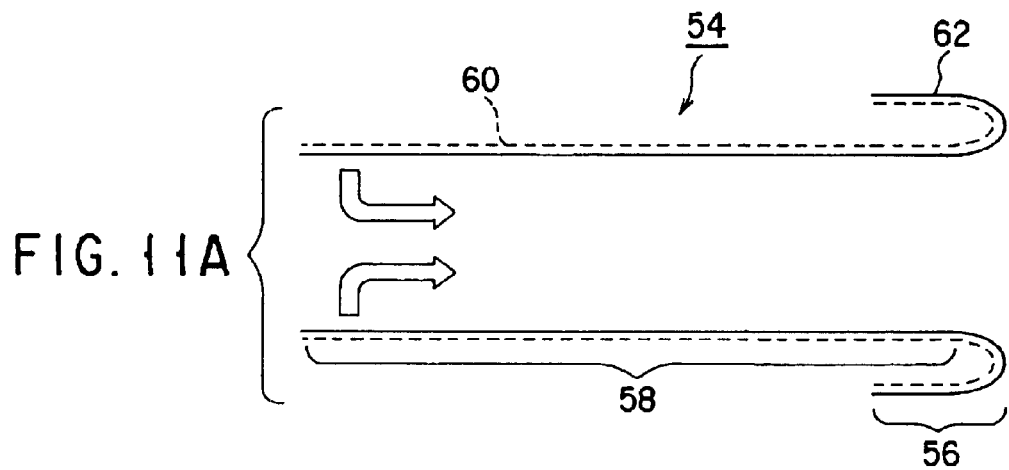
FIG. 11A is an axial sectional view showing a plain-stitched wire according to a fifth embodiment designed so that face-side loops appear on its outer peripheral surface with the other portion than an end portion reversed.
Figure 11B:
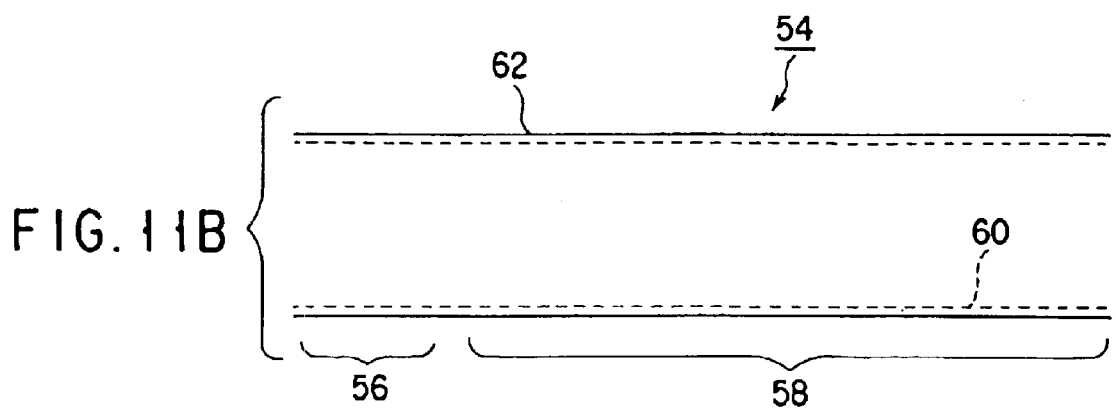
FIG. 11B is an axial sectional view showing a state in which the other portion than the end portion shown in FIG. 11A is restored to its original state such that reverse-side loops appear on the outer peripheral surface.

According to this embodiment, therefore, an end portion 56 of the stent 54 is previously subjected to shape-memory processing such the reverse-side loops 62 are obverse with the face-side loops 60 on the outer peripheral surface, as shown in FIG. 11A. In the stent 54 having the reverse-side loops 62 facing outward in the lumen, as shown in FIG. 11B, the end portion 56 subjected to shape-memory processing is made reluctant to be turned inside out with a small shock. Thus, the stent 54 can be prevented from being unexpectedly turned inside out as it is indwelled in the internal lumen.

Steps for manufacturing the stent 54 according to this embodiment will now be described with reference to FIGS. 11A and 11B.

The end portion 56 of the stent 54 that is knitted with the face-side loops 60 on the outside, as shown in FIGS. 7A and 7B, is turned inside out, and is subjected to shape-memory processing with the reverse-side loops 62 in its position facing outward, as shown in FIG. 11A. Thereafter, a portion 58 with the face-side loops 60 on the outside is turned inside out through the inside of the stent 54, as indicated by the arrows in FIG. 11A, so that the reverse-side loops 62 face outward throughout the length of the stent 54. The reverse-side loops 62 are covered entire with a filmy member (not shown) that can expand and contract in the diametrical direction and has a longitudinal length substantially equal to the length of the wire that has the reverse-side loops 62 facing outward. This filmy member is removable from the wire.

Although only the one end portion 56 is subjected to shape-memory processing for prevention of reversal, both end portions may alternatively be subjected to the same shape-memory processing.

When the stent 54 of this embodiment manufactured in this manner is indwelled in the lumen, it is designed to resist being turned inside out, as mentioned before. On the other hand, the end portion 56 is reversed inward as it is drawn into the stent 54 by means of the holding forceps 40 shown in FIG. 8A, for example. Thus, the stent 54 can be easily turned inside out when being recovered.

The stent 54, like the stents 2 and 27 according to the first and second embodiments, can be indwelled in the lumen. The inner catheter 17 of the stent delivery system 20 shown in FIG. 3A is inserted into the stent 54. If the stent 54 is fitted in the outer sheath 21, the plain-stitched wire, along with the filmy member, is pressed and contracted diametrically inward. If the stent 54 is released from the stent delivery system 20, as shown in FIG. 3A, it is rendered self-expanded outward in the diametrical direction of the lumen and indwelled in the narrow segment 22 in a dilated state, as shown in FIG. 3B. Thus, the stent 54 presses the inner wall (mucous membrane) in the lumen, thereby dilating the lumen diametrically outward.

The following is a description of processes for recovering the stent 54 expanded in this manner. Since the end portion 56 of the stent 54 is shaped, as mentioned before, the whole stent 54 cannot be unexpectedly turned inside out with ease. If the end portion 56 is reversed toward the inside of the stent 54 by means of the holding forceps 40 shown in FIG. 8A, for example, as it is recovered, as described in detail in connection with the second embodiment, the portions 58 other than the end portion 56 can be relatively easily turned inside out to allow the stent 54 to be recovered as the end portion 56 is drawn into the stent 54.

In recovering the stent 54 of this embodiment shown in FIG. 11B that is indwelled in the lumen, as in the case of the second embodiment, therefore, the stent 54 is gradually separated in the direction perpendicular to the mucous membrane from the side of the end portion (distal end) 56. Thus, the possibility of the stent 54 rubbing against the mucous membrane in the lumen can be lowered in an initial stage of turning the stent 54 inside out, so that the burden on the lumen can be lightened. As the separation from the mucous membrane advances, the area of contact between the stent 54 and the mucous membrane decreases. Even if the stent 54 heavily adheres to the mucous membrane, therefore, it can be separated and recovered relatively easily.

Although the processes for recovering the stent from the lumen have been described in connection with the first to fifth embodiments, the stent according to the present invention need not always be a stent to which the aforesaid processes of recovery is applicable, and the invention may be applied to any stent that can be recovered by being turned inside out.

According to the first to fifth embodiments, as described above, the distal side of the stent is drawn into the stent itself to be turned inside out when being recovered. As the stent is turned inside out, therefore, the area of contact between the stent and the mucous membrane decreases, and the stent is separated diametrically inward (or vertically) from the mucous membrane.

Since the stent can be easily separated from the mucous membrane, therefore, it can be also recovered with ease. Since there is little possibility of the stent rubbing against the mucous membrane when being recovered, moreover, the burden on the lumen can be minimized. Thus, the stent according to each of the embodiments described herein is particularly effective if it needs to be indwelled in the lumen for a long period of time.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A stent for dilating an internal lumen, comprising tubular segments capable of expanding and contracting in the radial direction thereof and having an axial length shorter than the expanded-state radius thereof, the segments being arranged side by side from a distal side to a proximal side in the axial direction of the stent, wherein each of segments is formed of a wire having a plain-stitch structure with reverse-side loops facing outward.

2. A stent according to claim 1, wherein at least one of the segments located individually on the distal and proximal sides is subjected to shape-memory processing such that face-side loops face outward.

3. A stent according to claim 1, wherein the segments are enclosed by a filmy member capable of expanding and contracting in the diametrical direction.

4. A stent according to claim 3, wherein the filmy member is made from bio-absorbable material.

5. A stent according to claim 1, wherein one of the segments located on the extreme distal side is connected with a pulling element extending on the proximal side of the segment on the extreme proximal side, the pulling element being passed through the interior of the segments.

6. A stent for dilating an internal lumen, comprising tubular segments capable of expanding and contracting in the radial direction thereof and having an axial length shorter than the expanded-state radius thereof, the segments being arranged side by side from a distal side to a proximal side in the axial direction of the stent, the stent further having a connecting portion capable of connecting each segment to another segment adjacent thereto and preventing interference between the segments so that the distal-side segment is turned back into the proximal-side segment, wherein the segments are enclosed by a filmy member capable of expanding and contracting in the diametrical direction and the filmy member is made from bio-absorbable material.

7. A stent for dilating an internal lumen, comprising tubular segments capable of expanding and contracting in the radial direction thereof and having an axial length shorter than the expanded-state radius thereof, the segments being arranged side by side from a distal side to a proximal side in the axial direction of the stent, the stent further having a connecting portion capable of connecting each segment to another segment adjacent thereto and preventing interference between the segments so that the distal-side segment is turned back into the proximal-side segment, wherein the segments are enclosed by a filmy member capable of expanding and contracting in the diametrical direction and one of the segments located on the extreme distal side is connected with a pulling portion extending on the proximal side of the segment on the extreme proximal side, the segments being arranged side by side when the stent is indwelled in the internal lumen, the pulling element being passed through the interior of the segments.

8. A stent according to claim 7, wherein one of the segments located on the extreme distal side is provided with a looped member connected with the pulling portion.

9. A stent according to claim 7, wherein each of the segments is formed of a zigzagged wire.

10. A stent for dilating an internal lumen, comprising tubular segments capable of expanding and contracting in the radial direction thereof and having an axial length shorter than the expanded-state radius thereof, the segments being arranged side by side from a distal side to a proximal side in the axial direction of the stent, the stent further having a connecting portion capable of connecting each segment to another segment adjacent thereto and preventing interference between the segments so that the distal-side segment is turned back into the proximal-side segment, wherein one of the segments located on the extreme distal side is connected with a pulling element extending on the proximal side of the segment on the extreme proximal side, the segments being arranged side by side when the stent is indwelled in the internal lumen, the pulling element being passed through the interior of the segments.

11. A stent according to claim 10, wherein one of the segments located on the extreme distal side is provided with a looped member connected with the pulling portion.

12. A stein for dilating an internal lumen, comprising tubular segments capable of expanding and contracting in the radial direction thereof and having an axial length shorter than the expanded-state radius thereof, the segments being arranged side by side from a distal side to a proximal side in the axial direction of the stent the stent further comprising a tubular filmy member located around the segments and capable of being urged to expand diametrically outward by the segments, wherein one of the segments located on the extreme distal side is connected with a pulling element extending on the proximal side of the segment on the extreme proximal side, the segments being arranged side by side when the stent is indwelled in the an internal lumen, the pulling element capable of being passed through the interior of the segments.

13. A stent according to claim 12, wherein one of the segments located on the extreme distal side is provided with a looped member connected with the pulling portion.

14. A recovery method for recovering a stent in a dilated state, indwelled in a detention portion in an internal lumen, comprising:
  inserting an intracoelomic observation system, having a channel and capable of observing the interior of a body cavity, into the body cavity;
  guiding a device having a holding mechanism through the channel of the intracoelomic observation system into the detention portion of the stent including tubular segments capable of expanding and contracting in the axial direction thereof and having an axial length shorter than the expanded-state radius thereof, the segments being arranged side by side from the distal side to the proximal side in the axial direction;
  holding that one of the segments of the stent located on the extreme distal side by means of the device passed through the segments; and
  pulling the device to the hand side to separate the segment on the extreme distal side while contracting the segment diametrically inward, and turning the stent inside out as the distal-side segment is passed through the interior of the successively adjacent segments on the proximal side, thereby separating and recovering the stent.

15. A recovering method for recovering a stent located in a living body, the stent comprising a filmy member and a plurality of tubular segments each having a length in an axial direction of the stent which is smaller than a radius of said each segment, the segments being arranged at regular intervals in an axial direction of the stent,
  inserting a holding member for holding a furthest one of the segments with respect to a proximal side, into an inside-diameter section of the stent;

making the holding member hold the furthest one of the segments, and pulling the holding member toward an extreme proximal side of the stent, and successively pulling and reversing the segments from the furthest one of the segments by further pulling the holding member, such that said each segment is passed through an interior of one of the segments which is located adjacent to said each segment and closer to the proximal side than said each segment.

16. A recovering method for recovering a stent located in a living body, the stent comprising a filmy member, a plurality of tubular segments each having a length in an axial direction of the stent, which is smaller than a radius of said each segment, the segments being arranged at regular intervals in the axial direction, and a pulling portion which is connected to a furthest one of the segments with respect to a proximal side, and extends to a position which is closer to the proximal side than a closet one of the segments, the furthest one of the segments and the closest one of the segments are located furthest from and closest to the proximal side when the stent is located in the loving body, moving a holding member capable of holding the pulling portion closer to the stent, making the holding member hold the pulling portion, the pulling portion toward the proximal side;

successively pulling and reversing the segments by further pulling the pulling portion, such that said each segment is passed through an interior of one of the segments which is located adjacent to said each segment, and closer to the proximal side than said each segment.

17. A stent comprising:

a filmy member;

a plurality of segments arranged in the filmy member, and a connecting portion capable of connecting each of the plurality of segments to another of the plurality of segments adjacent thereto and capable of preventing interference between the plurality of segments so that a distal-side segment is turned back into a proximal-side segment;

wherein each of the segments is tubular, and has a length which is smaller than a radius of said each segment, and the segments are arranged at regular intervals in an axial direction of the stent.

18. A stent according to claim 17, wherein each of the plurality of segments is formed of a wavy wire and the plurality of segments are enclosed by the filmy member capable of expanding and contracting in the diametrical direction.

19. A stent according to claim 17, wherein the plurality of segments are enclosed by the filmy member which is capable of expanding and contracting in the diametrical direction.

20. A stent according to claim 17, wherein the filmy member is provided to cover outer peripherals of the segments.

21. A stent according to claim 17, wherein said each segment is capable of expanding/contracting in a diametrical direction of said each segment.

22. A stent according to claim 17, wherein said filmy member expands/contracts when said each segment expands/contracts in the diametrical direction.

23. A stent according to claim 17, wherein the filmy member is made of bio-absorbable material.

24. A stent according to claim 17, wherein one of the plurality of segments which is located on an extreme distal side of the stent is connected with a pulling element extending through interiors of the segments to a position which is closer to a proximal side than one of the segments which is located on an extreme proximal side of the stent and wherein a looped member is provided at said one of the plurality of segments which is located on the extreme distal side of the stent, and the pulling element is connected to the looped member.

25. A stent comprising:

a filmy member, and a plurality of segments arranged in the filmy member, wherein each of the segments is tubular, and has a length which is smaller than a radius of said each segment, and the segments are arranged at regular intervals in an axial direction of the stent and wherein one of segments which is located on an extreme distal side of the stent is connected with a pulling element extending through interiors of the segments to a position which is closer to a proximal side than one of the segments which is located on an extreme proximal side of the stent.

26. A stent according to claim 25, wherein each of the plurality of segments is formed of a wavy wire and the plurality of segments are enclosed by the filmy member capable of expanding and contracting in the diametrical direction.

27. A stent according to claim 25, wherein the plurality of segments are enclosed by the filmy member which is capable of expanding and contracting in the diametrical direction.

28. A stent according to claim 25, wherein the filmy member is provided to cover outer peripherals of the segments.

29. A stent according to claim 25, wherein said each segment is capable of expanding/contracting in a diametrical direction of said each segment.

30. A stent according to claim 25, wherein said filmy member expands/contracts when said each segment expands/contracts in the diametrical direction.

31. A stent according to claim 25, wherein the filmy member is made of bio-absorbable material.

32. A stent according to claim 25, wherein a looped member is provided at said one of the plurality of segments which is located on the extreme distal side of the stent, and the pulling element is connected to the looped member.

33. A stent comprising:

a filmy member; and a plurality of segments arranged in the filmy member, wherein each of the segments is tubular, and has a length which is smaller than a radius of said each segment, and the segments are arranged at regular intervals in an axial direction of the stent, and wherein the segments and capable of preventing interference preventing the plurality of segments so that a distal-side segment is turned back into a proximal-side segment.

34. A stent according to claim 33, wherein each of the plurality of segments is formed of a wavy wire and the plurality of segments are enclosed by the filmy member capable of expanding and contracting in the diametrical direction.

35. A stent according to claim 33, wherein the plurality of segments are enclosed by the filmy member which is capable of expanding and contracting in the diametrical direction.

36. A stent according to claim 33, wherein the filmy member is provided to cover outer peripherals of the segments.

37. A stent according to claim 33, wherein said each segment is capable of expanding/contracting in a diametrical direction of said each segment.

38. A stent according to claim 33, wherein said filmy member expands/contracts when said each segment expands/contracts in the diametrical direction.

39. A stent according to claim 33, wherein the filmy member is made of bio-absorbable material.

40. A stent according to claim 33, wherein one of the plurality of segments which is located on an extreme distal side of the stent is connected with a pulling element extending through interiors of the segments to a position which is closer to a proximal side than one of the segments which is located on an extreme proximal side of the stent.

41. A stent according to claim 33, wherein a looped member is provided at said one of the plurality of segments which is located on the extreme distal side of the stent, and the pulling element is connected to the looped member.

* * * * *